US 6,720,448 B2

(12) United States Patent
Broccatelli

(10) Patent No.: US 6,720,448 B2
(45) Date of Patent: Apr. 13, 2004

(54) METHOD OF RECOVERING CHEMICAL SPECIES BY DEPOLYMERIZATION OF POLY (ETHYLENE TEREPHTHALATE) AND RELATED USE

(76) Inventor: Massimo Broccatelli, Via Petrarca 6, 06083 Bastia Umbra (Perugia) (IT)

( * ) Notice: Subject to any disclaimer, the term of this patent is extended or adjusted under 35 U.S.C. 154(b) by 46 days.

(21) Appl. No.: 09/967,929

(22) Filed: Oct. 2, 2001

(65) Prior Publication Data

US 2002/0065430 A1 May 30, 2002

(30) Foreign Application Priority Data

Oct. 11, 2000 (EP) .............................. 00830665

(51) Int. Cl.$^7$ ................ C07C 51/09; C07C 51/42; C07C 67/48; C07C 27/02
(52) U.S. Cl. .............. 562/483; 560/78; 562/480; 562/485; 562/486; 562/487; 568/858
(58) Field of Search ................. 562/483, 480, 562/485, 486, 487; 568/858; 560/78

(56) References Cited

U.S. PATENT DOCUMENTS

| 5,254,666 | A |   | 10/1993 | Benzaria |
| 5,430,174 | A |   | 7/1995 | Shono et al. |
| 5,545,746 | A |   | 8/1996 | Benzaria et al. |
| 6,075,163 | A | * | 6/2000 | Roh et al. .................. 562/483 |

FOREIGN PATENT DOCUMENTS

| DE | 195 34 276 A1 | 3/1997 |
| DE | 196 29 042 A1 | 1/1998 |
| EP | 0 597 751 A1 | 5/1994 |
| WO | WO 95/27753 | 10/1995 |
| WO | WO 98/03459 | 1/1998 |
| WO | WO 99/28285 | 6/1999 |

OTHER PUBLICATIONS

English Language Abstract of DE 195 34 276.
English Language Abstract of EP 0 597 751.
European Search Report for EP 00830665.6 (priority document).
Co–pending U.S. application No. 09/792,567; Title: Method of Recovery of Terephthalic Acid from a Material Containing Poly (Ethylene Terephthalates) Inventor: Massimo Broccatelli U.S. Filing Date: Feb. 21, 2001.

* cited by examiner

Primary Examiner—Alan L. Rotman
Assistant Examiner—Taylor Victor Oh
(74) Attorney, Agent, or Firm—James B. Conte; Barnes & Thornburg

(57) ABSTRACT

The present invention relates to a method of recovering a solution comprising the chemical species obtained by depolymerization of PET from a material containing poly (ethylene terephthalate) in the form of bottles, by making said material react, in the absence of water, with a reagent consisting of one or more metal salts of a weaker acid than the terephthalic acid and of ethylene glycol, until a water-soluble intermediate product is obtained, and subsequently carrying out dissolution in water, stirring and filtering.

21 Claims, No Drawings

METHOD OF RECOVERING CHEMICAL SPECIES BY DEPOLYMERIZATION OF POLY (ETHYLENE TEREPHTHALATE) AND RELATED USE

BACKGROUND OF THE INVENTION

1. Field of the Invention

The present invention relates to a method of recovering chemical species by depolymerization of poly(ethylene terephthalate) from a material containing poly(ethylene terephthalate). In particular, the present invention relates to a method of obtaining an aqueous solution comprising chemical species from depolymerization of poly(ethylene terephthalate), for instance in the form of bottles or other manufactured articles coming from a differentiated salvage dump.

In addition, the present invention relates to use of said chemical species from depolymerization of poly(ethylene terephthalate) in the processes for producing regenerated poly(ethylene terephthalate).

2. Prior Art

Known in the art is the existence of some chemical methods involving recovery of terephthalic acid or fragments of polymers of the poly(ethylene terephthalate) type starting from materials containing poly(ethylene terephthalate).

Poly(ethylene terephthalate) also identified by the abbreviation (PET) is a saturated polyester resin obtained from terephthalic acid (TPA) and ethylene glycol (EG). PET is a material widely used in the textile field and in the food-industry packaging sector and in particular in the manufacture of bottles for soft drinks.

Due to its large use, an increasingly growing interest in poly(ethylene terephthalate) (PET) recycling has been developed in the most recent years.

Substantially chemical methods of recovering useful substances for preparing poly(ethylene terephthalate), such as the terephthalic acid or fragments of polymers of the poly (ethylene terephthalate) (PET) type are distinguishable from each other due to the mechanism used which can belong to one of the following main categories: alcoholysis, glycolysis, acid hydrolysis, neutral hydrolysis and alkaline hydrolysis.

Obviously, each individual mechanism can find application through various techniques differing from each other due, for example, to a different number of phases, different temperatures, pressures, involved reagents, reaction solvents.

The chemical method utilizing alcoholysis brings to formation of bis or poly(alkyl)terephthalates, whereas glycolysis produces bis or poly(hydroxyethyl)terephthalates that are chemical intermediates in the production of poly (ethylene terephthalate) by known processes of trans-esterification.

The chemical method utilizing acid hydrolysis is carried out by making PET react with a large excess of a strong acid in solution, sulfuric acid for example.

The sulfuric acid acts in a very short period of time, say some minutes, at a temperature included between room temperature and 95° C., by dissolving the starting PET with formation of terephthalic acid (TPA). The chemical method utilizing acid hydrolysis is scarcely applied in the industrial field, mainly due to the high corrosiveness of the reaction system and also due to the huge amount of salt solution produced for neutralizing the employed acid.

The chemical method utilizing neutral hydrolysis is conducted by treating PET with water or steam, under pressure at a temperature included between 200 and 300° C., in the presence of appropriate catalysts. This method too has some drawbacks. The main disadvantages of this technology are represented by high energy consumptions and the impossibility of eliminating all mechanical impurities from the terephthalic acid (TPA) obtained by precipitation, such as undissolved particles and insoluble polymers originally present in the starting material.

Finally, the chemical method utilizing alkaline hydrolysis is almost always carried out by use of alkaline hydroxides or ammonium hydroxides.

Use of these bases leads to formation of aqueous solutions of the corresponding salt of the terephthalic acid (TPA). These solutions can be easily cleared from mechanical impurities by filtering, flocculating or settling processes. In addition, terephthalic acid (TPA) is recovered from said aqueous solutions by precipitation in an acid medium.

Of all the above mentioned methods, the method utilizing alkaline hydrolysis has recently found many applications. Some of them are reproduced hereinafter:

- a first application contemplates treatment of PET with a concentrated solution of an alkaline hydroxide, under pressure and at temperatures close to or higher than 250° C. The PET/alkaline solution ratio is greater than 20.
- a second application contemplates treatment of PET with a stoichiometric amount of an alkaline hydroxide in ethylene glycol (EG) at a temperature included between 100 and 200° C. If an ammonium hydroxide is used as the base, the method is carried out under pressure. In both cases, at all events, the obtained reaction mixture is dissolved in water.

Finally, a third application provides for PET to be extruded in the presence of hydroxide at temperatures higher than 250° C. Subsequently, the obtained salt is dissolved in an aqueous solution.

Generally problems resulting from use of alkaline or alkaline-earth hydroxides or from use of concentrated solutions of such hydroxides are well known. By alkaline hydroxides it is meant a sodium hydroxide for example, by alkaline-earth hydroxide it is for example meant a calcium hydroxide.

The main disadvantages are connected with difficulties in manipulating these types of very aggressive reagents by the operators. In addition, modifications in the plants are required to be adopted together with a series of technical expedients in plant construction due to the big problems connected with corrosion of these reagents, above all if used in solution.

In the above first application, disadvantages consist in being obliged to heat, filter and recover great amounts of solution. In addition, in this application use of great amounts of hydroxides and adoption of high pressures is provided.

In the above second and third applications, the main disadvantage resides in the fact that it is impossible to obtain terephthalic acid (TPA) free from undesirable yellow-pink colorations. In fact, in the absence of water the hydroxides employed at temperatures higher than 100° C. react with the ethylene glycol (EG) resulting from the hydrolysis reaction. The reaction between hydroxides and ethylene glycol brings to formation of strongly red-colored and water-soluble products. Formation of these colored compounds inhibits precipitation of white TPA or of uncontaminated chemical species from depolymerization of the poly(ethylene terephthalate). Therefore, the terephthalic acid (TPA) containing colored impurities must be bleached. The methods reproduced in literature for TPA bleaching for example are long and expensive. For instance, some bleaching methods involve extraction of impurities by use of water-insoluble higher alcohols.

Therefore there is a need for a method of recovering substances useful in the production of regenerated poly (ethylene terephthalate) from a material containing poly (ethylene terephthalate) coming for example from a differentiated salvage dump. These substances can be terephthalic acid or chemical species from depolymerization of poly (ethylene terephthalate) having a reduced molecular weight as compared with the poly(ethylene terephthalate) polymer present in the starting material.

In particular, a method is required which enables recovery of uncontaminated terephthalic acid or chemical species in the form of polymeric fragments of the poly(ethylene terephthalate) type, free from colored contaminations and impurities.

Still more particularly, there is a need for a method of recovering terephthalic acid or polymeric fragments of poly (ethylene terephthalate) having a reduced molecular weight by a process that does not involve use of alkaline hydroxides, alkaline-earth hydroxides and ammonium hydroxide or concentrated solutions of these hydroxides.

In addition, there is a requirement for a method of recovering terephthalic acid or polymeric fragments of poly (ethylene terephthalate) having a reduced molecular weight as compared with the poly(ethylene terephthalate) polymer present in the starting material, which is cheap and advantageous.

SUMMARY OF THE INVENTION

One of the aims of the present invention is to provide a method of recovering substances useful in the production of poly(ethylene terephthalate), such as terephthalic acid or chemical species from depolymerization of PET, with a reduced molecular weight as compared with the PET polymer present in the starting material.

Another aim of the present invention is to provide a method of recovering terephthalic acid or polymeric fragments of poly(ethylene terephthalate) devoid of colored contaminations starting from a material containing poly (ethylene terephthalate).

A further aim of the invention is to provide a method of recovering terephthalic acid or polymeric fragments of poly (ethylene terephthalate) that does not use alkaline hydroxides, alkaline-earth hydroxides and ammonium hydroxide or concentrated solutions of these hydroxides.

The foregoing and still further aims that will also become more apparent during the following detailed description have been achieved by the Applicant that has surprisingly found out that recovery of an aqueous solution comprising soluble chemical species obtained from depolymerization of PET having a reduced molecular weight as compared with the poly(ethylene terephthalate) present in the starting material is possible and advantageous.

In particular, the Applicant has found that it is possible and advantageous to precipitate in an undissociated form (not salified form) substances such as the terephthalic acid (TPA) and chemical species in the form of polymeric fragments of PET of a reduced molecular weight from said solution comprising the chemical species from depolymerization of PET.

In addition, the Applicant has found it useful to employ said substances in the processes for producing regenerated poly(ethylene terephthalate).

The Applicant has also found that materials containing poly(ethylene terephthalate), for example waste materials in the form of bottles or other manufactured articles coming from a differentiated salvage dump, can be reacted by mixing them, in the absence of water, with ethylene glycol and a reagent consisting of one or more metal salts of weaker acids than the terephthalic acid, until a water-soluble intermediate reaction product is obtained. Said intermediate reaction product comprises the chemical species from depolymerization of poly(ethylene terephthalate) in a salified form and therefore in a soluble form and possible parts of unreacted PET or parts of material of different nature from PET which are present in the waste material.

Accordingly, it is an object of the present invention to provide a method of recovering, from a material containing PET, an aqueous solution comprising the soluble chemical species from depolymerization of PET, the essential features of which are defined in the main claim 1.

A preferred embodiment of the present invention is a method of recovering terephthalic acid from said aqueous solution comprising the soluble chemical species obtained from depolymerization of PET, the features of which are defined in the appended dependent claims.

It is a further preferred embodiment of the present invention a method of recovering, by precipitation, the chemical species from depolymerization of PET in an undissociated form from said aqueous solution, the features of which are defined in the appended dependent claims.

It is a further object of the present invention to provide use of said terephthalic acid or said polymeric fragments of PET having a reduced molecular weight, in the production of regenerated poly(ethylene terephthalate).

Other preferred embodiments of the present invention are described in the appended dependent claims.

Further technical features and the advantages of the present invention will be best understood from the following detailed description.

DESCRIPTION OF THE PREFERRED EMBODIMENTS

In accordance with the present invention, the starting material containing poly(ethylene terephthalate) (PET), for instance waste material in the form of unbroken bottles or small fragments, fibers, ground scraps or films is put in a mixer device, in the absence of water.

The mixer device can be of the type providing mechanical or electrical operation. Preferably, in a preferred embodiment it can be a reactor equipped with a stirrer or, alternatively, it can be a propeller reactor, the propeller being anchored to the device bottom. The propeller preferably rotates at a speed adapted to enable grinding of the starting material and cause heating by friction of same. The mixing speed is preferably included between 300 and 1600 revolutions per minute (rpm). Preferably, it is included between 800 and 1500 rpm. Advantageous results were achieved at a speed included between 900 and 1450 rpm.

Added to the starting material is a reagent in a solid form, so that the whole mixture forms a reaction mixture in the absence of water. Alternatively, the reagent can be added after a mechanical pre-treating step of the starting material.

The reagent used is made up of an anhydrous composition comprising one or more metal salts of weaker acids than the terephthalic acid. These metal salts must have a metallic cation capable of salifying one or more carboxyl and/or hydroxyl functions present in the chemical species from depolymerization of PET contained in the soluble intermediate reaction product. In addition, metal salts must have a metal cation capable of forming water-soluble TPA salts or water-soluble salified polymeric fragments in solution.

Practically, if the types of salts used are wished to be represented by a chemical formula, we can say that these salts are selected from a group consisting of salts having $M_nX_m$ (n=valence of anion X and m=valence of cation M) as the general chemical formula; wherein M=metal of valence m supplying water-soluble terephthalates such as for example sodium, potassium, zinc, antimony and tin; and X=anion of a weaker acid than the terephthalic acid.

The terephthalic acid has a pKa of 3.51. The dissociation constants pK1 and pK2 for the terephthalic acid at a temperature of 25° C. are 3.54 and 4.46, respectively.

As a reference parameter to establish the force of an acid, the value herein assumed is that of the dissociation constant of an acid in water, i.e. value of Ka or Kb, knowing that $Kw=Ka.Kb=10^{-14}$.

For instance, the acids that can be used in salts $M_nX_m$ are selected from inorganic weak acids such as $H_2CO_3$, $H_2S$, $HNO_2$, $H_3BO_4$, HClO, $H_3BO_3$ or from aliphatic organic acids (with the exclusion of formic acid and the acids alpha-substituted with electron-attractor groups like halogens, —OH, —SH, —CHO, —CRO, —CN, —COOH) such as acetic acid, propionic acid, acrylic acid, or aromatic acids such as benzoic acid, meta or para-toluic acid and acids having groups like —OH, —OR and —NH$_2$ as substituent in the aromatic ring. Further possible examples of salts $M_nX_m$, finding application in the method of the present invention are represented by: carbonates, bicarbonates, borates (orthoborates, metaborates, perborates and tetraborates), acetates, benzoates and salicylates.

Preferably used are sodium carbonate, potassium carbonate, sodium bicarbonate, potassium bicarbonate, sodium sulfide, sodium acetate, potassium acetate, antimony triacetate, zinc acetate and sodium tetraborate. Particularly advantageous results are obtained by use of sodium carbonate.

Preferably, mixtures of the above salts are used; for instance, the following mixtures have been found very advantageous: 50% $Na_2CO_3$/50% $K_2CO_3$, 50% $(CH_3COO)_3Sb$/50% $CH_3COONa$, 50% $(CH_3COO)_3Sb$/50% $(CH_3COO)_2Zn$.

Preferably, the reaction mixture in the mixing step comprises such an amount of reagent by weight that the equivalent of the metal or metals contained therein are included between 1 and 100% of the equivalents of TPA contained in the poly(ethylene terephthalate) present in the starting material, more preferably are included between 10 and 80% of the equivalents of TPA contained in the poly(ethylene terephthalate) present, most preferably are included between 40 and 60% of the equivalents of TPA contained in the poly(ethylene terephthalate) present.

Preferably, the reaction mixture comprises the material containing poly(ethylene terephthalate) and the ethylene glycol in a ratio included between 1:1 and 10:1; more preferably in a ratio included between 3:10 and 7:1; most preferably in a ratio included between 4:10 and 6:1.

The reaction mixture is mixed, under ambient pressure and in the absence of water, until by effect of the mechanical working the reaction mixture is changed to a water-soluble intermediate reaction product containing the chemical species from depolymerization of PET in a salified form.

The reaction mixture is mixed over a period of time preferably included between 5 and 200 minutes; more preferably over a period of time included between 10 and 140 minutes; most preferably over a period of time included between 15 and 100 minutes.

Following the mechanical working, the temperature within the device reaches the desired value, at ambient pressure.

Alternatively, heating means such as electric resistors, circulation of heating fluids, induction heaters and microwave ovens can be used. Preferably, the heating means is used to bring the reaction mixture to the desired temperature or, alternatively, to keep temperature constant to a given value.

Preferably, the temperature is included between 90 and 260° C.; more preferably values included between 95 and 220° C. and most preferably values included between 100 and 190° C. are involved.

Heating of the reaction mixture at the above temperatures takes place by mechanical action due to mixing of the reaction mixture in the mixing device. Alternatively, heating is obtained by external heating means.

The Applicant has surprisingly found that at the above operating conditions and process temperatures the PET-containing material present in the reaction mixture changes to an intermediate reaction product having the unexpected property of being highly water soluble.

Said intermediate product is water soluble because it comprises soluble chemical species from depolymerization in a salified form. The chemical species from depolymerization can be represented by polymeric fragments of the poly(ethylene terephthalate) polymer having a reduced molecular weight as compared with the untreated PET polymer, present in the starting material.

Said fragments have at least at one of the two terminations, a carboxyl group salified by the metal cation M employed whereas at the other termination they can have a salified carboxyl group, a carboxyl group not salified or alternatively an hydroxyl group, depending on how the PET polymer is fragmented.

The soluble chemical species from depolymerization are obtained following interaction between PET and said metal salts of weaker acids of the terephthalic acid. Possibly, the water-soluble reaction compound in addition to the chemical species also comprises portions of unreacted PET or part of material of different nature from PET, that are present in the starting material. Practically, the poly(ethylene terephthalate) is submitted to a "digestion" step, under ambient pressure and in the absence of water, with the $M_nX_m$ salts used. The reaction compound containing the intermediate product physically has a consistency varying between that of a slightly wet powder and that of a paste in a semi-solid state depending on the amounts of reagent and ethylene glycol therein used.

From a chemical point of view, it can be assumed that the poly(ethylene terephthalate) polymer, by interacting with the reagent and the ethylene glycol, reduces its average molecular weight giving rise to salified and consequently water-soluble fragments. The chains of smaller sizes that are formed have, at their terminations, one or more carboxyl groups at least one of which is salified with the reagent metals and consequently they are water-soluble.

Therefore, in accordance with the present invention, the water-insoluble starting material, following treatment with a solid reagent in the absence of water, is changed to a water-soluble intermediate product or compound because it consists of ionic species. Said soluble compound could contain the possibly unreacted portion of the ethylene glycol added in the mixing step. Alternatively, the intermediate product may comprise a portion of unreacted starting material.

The Applicant has surprisingly found that the ethylene glycol under these specific work conditions, does not produce colored contaminations that would pollute the final products.

Subsequently, the intermediate product obtained from the mixing step is brought into contact with a water portion.

Preferably, the water portion is in a ratio by weight included between 4 and 30 parts by weight of reaction mixture; preferably it is included between 8 and 25 parts; more preferably it is included between 10 and 20 parts of reaction mixture.

Next, the intermediate product is maintained under stirring for a period of time included between 10 and 100 minutes; more preferably for a period of time included between 20 and 60 minutes.

Following addition of water to the soluble intermediate reaction product, a solution is obtained. Said stirring step enables all chemical species from depolymerization present therein to be made soluble.

Finally, a subsequent filtering step enables the unreacted material portion to be separated from the solution.

The filtered water solution contains the soluble chemical species from depolymerization, in the form of salified polymeric fragments having a reduced molecular weight as compared with the PET polymer present in the starting material.

The range of the molecular weights owned by the polymeric fragments obtained by the method of the present invention cannot be evaluated in a precise manner because it is a depolymerization reaction of a PET polymer leading to obtaining fragments of sizes varying from each other to a great extent depending on how the reaction is conducted. The essential condition to be achieved, which represents the aim of the present invention, is that of obtaining soluble polymeric fragments, irrespective of the weight and sizes of the individual fragments.

Following addition of water to the soluble intermediate product and subsequent filtering, a solution is obtained which comprises ionic species from PET depolymerization obtained by interaction of PET with the metal salts of the reagent and the ethylene glycol and parts of said possibly unreacted metal salts and ethylene glycol.

Preferably, the filtered solution is submitted to the subsequent treatment steps.

The treatment steps differ from each other depending on the final product that is wished to be obtained.

In a first embodiment of the present invention the final product that is wished to be obtained is represented by PET fragments of low molecular weight having a non salified functional carboxyl group at least at one of their terminations. Said fragments, due to their chemical nature, could be defined poly(hydroxyethyl)terephthalates because they could be obtained by head-and-tail esterification of mono (hydroxyethyl)terephthalate monomers.

Added to the filtered solution is an amount of a stronger acid than TPA for the purpose of creating the suitable conditions to cause precipitation of said fragments. It has been noted that said precipitation takes place in an almost complete manner when the solution pH is lower than or equal to 7.

As the strong acids the following can be preferably employed: $H_2SO_4$, $HCl$, $HNO_3$, $H_3PO_4$ and $HCOOH$.

The precipitated polymeric fragments are subsequently separated from the liquid solution. Such a liquid portion will comprise: water, the salt of the strong acid added thereto to carry out acidification and the possibly unreacted ethylene glycol.

Preferably, the ethylene glycol possibly present in the aqueous phase can be recovered by fractional distillation.

Preferably, the chemical species from depolymerization that have not been previously precipitated and separated from the aqueous solution are submitted to a further washing step.

In a second embodiment of the present invention the final product that is wished to be obtained is terephthalic acid.

The filtered solution containing the chemical species from depolymerization of PET in a soluble salified form is submitted to hydrolysis following methods well-known in the art.

In a first case hydrolysis is carried out by heating and stirring of the solution. Following these two operations a solution is obtained which comprises part of terephthalic acid in solution because it is in a salified form and possibly part of precipitated terephthalic acid in an undissociated form because it is in a not salified form. Subsequently the obtained solution is added with a strong acid to obtain complete precipitation of the whole terephthalic acid.

In a second case, hydrolysis is carried out by addition of a basic reagent, heating and stirring of the solution. By these operating modalities a solution is obtained which comprises the whole terephthalic acid completely in a salified form.

Subsequently the solution is added with a portion of strong acid to obtain full precipitation of the terephthalic acid in an insoluble undissociated form.

The terephthalic acid obtained in accordance with the method of the present invention can be validly applied in the process for preparing a novel regenerated poly(ethylene terephthalate). Alternatively, also the polymeric fragments obtained in accordance with the method of the present invention can be validly employed to obtain regenerated poly(ethylene terephthalate) because these polymeric fragments are chain lengths of the poly(ethylene terephthalate) polymer. The advantage achieved by use of said polymeric fragments having a lower molecular weight than the starting poly(ethylene terephthalate) polymer, is given by the fact that they represent an intermediate stage in the polymerization process leading to formation of PET starting from TPA and ethylene glycol monomers and therefore their use involves saving of time and energy.

The method of the present invention has the following advantages as compared with the chemical processes for recovering substances useful in PET production, known in the art:

it enables recovery of poly(hydroxyethyl)terephthalates even starting from a material containing very polluted PET, since the polluting substances are not water-soluble and are removed by filtering, whereas the soluble fragments remain in the aqueous phase when they precipitate by acidification;

it enables recovery of TPA by less drastic hydrolysis processes because they are not carried out in the heterogeneous phase, which happens when PET is directly acted upon, but in the homogeneous phase on solutions of water-soluble products. This operating modality inhibits production of colored or polluting substances during the process and the possibility of carrying out hydrolysis without resorting to basic chemical agents;

it also represents a method of separating PET from other plastic materials often present in the starting material because these remain unchanged during the process.

One of the preferred embodiments of the present invention is given hereinafter, by way of example. This embodiment must not be considered as a limitation of the present invention.

EXAMPLES

The examples below, 1–75, have been carried out in two different reactors.

Reactor No. 1 consists of a cylinder with a diameter of 1 m and a height of 1.5 m, to the bottom of which a propeller rotating at a fixed speed of 1420 rpm is fastened. This reactor is equipped with heating resistors.

Reactor No. 2 consists of a cylinder with a diameter of 1 m and a height of 2.8 m, equipped with a propeller-stirrer having a speed varying between 300 and 600 rpm and with heating resistors.

Examples 1 to 60 were carried out in reactor No. 1 with the following modalities:

The reactor is loaded with 50 kg of PET bottles, from a differentiated salvage dump, which still hold PP caps and PE or paper labels, so that PET content in the charge is about 90% of the total amount=45 kg. Loading is carried out while the propeller is rotating, at ambient pressure, in the absence of water and with the heating resistors turned off.

The loaded material is left under very strong stirring for about 10 minutes, so that bottles are ground and heated by friction to about 100° C.

At this point a reagent is added which comprises one or more salts of weaker acids than TPA or mixtures of same in the absence or in the presence of ethylene glycol, already heated to the desired reaction temperature (100–190° C.), and the heating resistors are switched on to maintain said temperature, and the reaction is allowed to go on until it comes to an end.

When this mixing step is over, water is added which, by evaporating, cools the reaction mixture to a temperature below 100° C. At this point further water is added and the mixture is maintained under stirring at a temperature included between 40 and 99° C. until complete dissolution of the soluble species present in the reaction mixture is reached. The solution is filtered and sent to the stage of the poly(hydroxyethyl)terephthalate acidification and precipitation with a stronger acid than the terephthalic acid, such as $H_2SO_4$, HCl, $HN_3$, $H_3PO_4$, HCOOH.

Alternatively, the solution is filtered and submitted to neutral, acid or alkaline hydrolysis, the latter being carried out by acidification with a stronger acid than TPA, thereby obtaining a terephthalic acid (TPA) precipitate.

When this step is over, the process yields are measured by putting the residual solid content resulting from filtration into water, separating the supernatant portion (PP, PE, cellulose) from the bottom body (ground and unreacted PET), drying and weighing said bottom body. Practically the unreacted PET gives the yield value.

Examples 61 to 75 have been carried out in reactor No. 2.

In this reactor higher amounts of ethylene glycol are required to be used so that the reaction mixture may be conveniently stirred. In this case the reagents are simultaneously loaded and the reaction times are measured at the moment that the system reaches the desired reaction temperature by effect of heating exclusively due to the heating resistors (since in this case friction due to stirring produces negligible heat). Modalities are the same as in examples 1 to 60.

The results are reproduced in the Table below.

| Ex. No. | Salt or mixture of metal salts | kg of salt or mixture of metal salts | kg of ethylene glycol | Reaction temp. ° C. | Reaction time Minutes | Reacted PET % |
|---|---|---|---|---|---|---|
| 1 | $Na_2CO_3$ | 12,425 | 5 | 100 | 120 | 8 |
| 2 | $Na_2CO_3$ | 12,425 | 5 | 150 | 120 | 32 |
| 3 | $Na_2CO_3$ | 12,425 | 5 | 190 | 120 | 45 |
| 4 | $Na_2CO_3$ | 24,850 | 5 | 100 | 120 | 17 |
| 5 | $Na_2CO_3$ | 24,850 | 5 | 150 | 105 | 40 |
| 6 | $Na_2CO_3$ | 24,850 | 5 | 190 | 75 | 52 |
| 7 | $Na_2CO_3$ | 36,000 | 5 | 100 | 120 | 25 |
| 8 | $Na_2CO_3$ | 36,000 | 5 | 150 | 90 | 50 |
| 9 | $Na_2CO_3$ | 36,000 | 5 | 190 | 60 | 60 |
| 10 | $Na_2CO_3$ | 12,425 | 15 | 100 | 33 | 60 |
| 11 | $Na_2CO_3$ | 12,425 | 15 | 150 | 19 | 72 |
| 12 | $Na_2CO_3$ | 12,425 | 15 | 190 | 14 | 80 |
| 13 | $Na_2CO_3$ | 24,850 | 15 | 100 | 30 | 63 |
| 14 | $Na_2CO_3$ | 24,850 | 15 | 150 | 15 | 74 |
| 15 | $Na_2CO_3$ | 24,850 | 15 | 190 | 11 | 82 |
| 16 | $Na_2CO_3$ | 36,000 | 15 | 100 | 27 | 65 |
| 17 | $Na_2CO_3$ | 36,000 | 15 | 150 | 12 | 77 |
| 18 | $Na_2CO_3$ | 36,000 | 15 | 190 | 9 | 85 |
| 19 | $Na_2CO_3$ | 12,425 | 30 | 100 | 30 | 65 |
| 20 | $Na_2CO_3$ | 12,425 | 30 | 150 | 15 | 79 |
| 21 | $Na_2CO_3$ | 12,425 | 30 | 190 | 9 | 88 |
| 22 | $Na_2CO_3$ | 24,850 | 30 | 100 | 25 | 67 |
| 23 | $Na_2CO_3$ | 24,850 | 30 | 150 | 12 | 80 |
| 24 | $Na_2CO_3$ | 24,850 | 30 | 190 | 7 | 90 |
| 25 | $Na_2CO_3$ | 36,000 | 30 | 100 | 20 | 70 |
| 26 | $Na_2CO_3$ | 36,000 | 30 | 150 | 9 | 83 |
| 27 | $Na_2CO_3$ | 36,000 | 30 | 190 | 5 | 92 |
| 28 | $Na_2CO_3$ | 12,425 | 70 | 100 | 25 | 67 |
| 29 | $Na_2CO_3$ | 12,425 | 70 | 150 | 13 | 82 |
| 30 | $Na_2CO_3$ | 12,425 | 70 | 190 | 6 | 90 |
| 31 | $Na_2CO_3$ | 24,850 | 70 | 100 | 23 | 69 |
| 32 | $Na_2CO_3$ | 24,850 | 70 | 150 | 11 | 84 |
| 33 | $Na_2CO_3$ | 24,850 | 70 | 190 | 6 | 92 |
| 34 | $Na_2CO_3$ | 36,000 | 70 | 100 | 16 | 72 |
| 35 | $Na_2CO_3$ | 36,000 | 70 | 150 | 8 | 85 |
| 36 | $Na_2CO_3$ | 36,000 | 70 | 190 | 5 | 94 |
| 37 | $K_2CO_3$ | 16,200 | 5 | 100 | 120 | 7,5 |
| 38 | $K_2CO_3$ | 32,400 | 5 | 150 | 115 | 42 |
| 39 | $K_2CO_3$ | 48,500 | 5 | 190 | 60 | 60 |
| 40 | $K_2CO_3$ | 32,400 | 15 | 190 | 12 | 78 |
| 41 | $K_2CO_3$ | 32,400 | 30 | 190 | 8 | 88 |
| 42 | $K_2CO_3$ | 32,400 | 70 | 190 | 7 | 90 |
| 43 | $K_2CO_3$ | 48,500 | 70 | 190 | 69 | 92 |
| 44 | $Na_2CO_3$ | 39,400 | 5 | 190 | 80 | 55 |
| 45 | $Na_2CO_3$ | 39,400 | 15 | 190 | 110 | 78 |
| 46 | $Na_2CO_3$ | 39,400 | 30 | 190 | 7 | 98 |
| 47 | $Na_2CO_3$ | 39,400 | 70 | 190 | 6 | 90 |
| 48 | 50% $Na_2CO_3$ - 50% $K_2CO_3$ | 28,650 | 5 | 190 | 75 | 50 |
| 49 | 50% $Na_2CO_3$ - 50% $K_2CO_3$ | 28,650 | 15 | 190 | 10 | 80 |
| 50 | 50% $Na_2CO_3$ - 50% $K_2CO_3$ | 28,650 | 30 | 190 | 8 | 90 |
| 51 | 50% $Na_2CO_3$ - 50% $K_2CO_3$ | 28,650 | 70 | 190 | 7 | 91 |
| 52 | $Na_2S$ | 18,300 | 30 | 190 | 10 | 85 |
| 53 | $CH_3COONa$ | 19,300 | 30 | 190 | 15 | 80 |
| 54 | $CH_3COONa$ | 39,500 | 30 | 190 | 12 | 85 |
| 55 | $(CH_3COO)_3Sb$ | 46,500 | 15 | 190 | 14 | 89 |
| 56 | $(CH_3COO)_3Sb$ | 46,500 | 30 | 190 | 9 | 91 |
| 57 | 50% $(CH_3COO)_3Sb$ - 50% CH3COONa | 37,000 | 15 | 190 | 12 | 88 |
| 59 | 50% $(CH_3COO)_3Sb$ - 50% $(CH_3COO)_2Zn$ | 66,000 | 30 | 190 | 8 | 94 |
| 60 | $(CH_3COO)_2Zn$ | 43,000 | 30 | 190 | 9 | 95 |
| 61 | $Na_2CO_3$ | 12,425 | 150 | 100 | 35 | 85 |
| 62 | $Na_2CO_3$ | 24,850 | 150 | 150 | 15 | 90 |

-continued

| Ex. No. | Salt or mixture of metal salts | kg of salt or mixture of metal salts | kg of ethylene glycol | Reaction temp. °C. | Reaction time Minutes | Reacted PET % |
|---|---|---|---|---|---|---|
| 63 | $Na_2CO_3$ | 36,000 | 150 | 190 | 10 | 92 |
| 64 | $K_2CO_3$ | 16,200 | 150 | 100 | 35 | 83 |
| 65 | $K_2CO_3$ | 32,400 | 150 | 150 | 15 | 88 |
| 66 | $K_2CO_3$ | 48,500 | 150 | 190 | 10 | 90 |
| 67 | $NaHCO_3$ | 19,700 | 150 | 100 | 35 | 83 |
| 68 | $NaHCO_3$ | 39,400 | 150 | 150 | 15 | 90 |
| 69 | $NaHCO_3$ | 59,500 | 150 | 190 | 10 | 92 |
| 70 | 50% $Na_2CO_3$ - 50% $K_2CO_3$ | 14,400 | 150 | 100 | 35 | 84 |
| 71 | 50% $Na_2CO_3$ - 50% $K_2CO_3$ | 28,650 | 150 | 150 | 15 | 89 |
| 72 | 50% $Na_2CO_3$ - 50% $K_2CO_3$ | 43,000 | 150 | 190 | 10 | 90 |
| 73 | $CH_3COONa$ | 39,500 | 150 | 150 | 15 | 90 |
| 74 | $(CH_3COO)_3Sb$ | 46,500 | 150 | 150 | 15 | 90 |
| 75 | $(CH_3COO)_2Zn$ | 43,000 | 150 | 190 | 10 | 95 |

What is claimed is:

1. A method of recovering terephthalates from a non-water soluble material containing poly(ethylene terephthalate) (PET), comprising;
   mixing, in the absence of water said non-water soluble material containing poly(ethylene terephthalate), ethylene glycol and one or more water-soluble salts of acids weaker than terephthalic acid but stronger than water, until a plurality of water soluble polymeric fragments, wherein said polymeric fragments are from the poly(ethylene terephthalate); and
   mixing water with the water soluble polymeric fragments to provide a solution including said polymeric fragments mixed with water.

2. The method as claimed in claim 1, wherein the water soluble salts are selected from the group consisting of: sodium carbonate, potassium carbonate, sodium bicarbonate, potassium bicarbonate, sodium sulfide, sodium acetate, potassium acetate, sodium propionate, potassium propionate, sodium benzoate, potassium benzoate, zinc acetate, antimony triacetate, sodium tetraborate, and mixtures thereof.

3. The method as claimed in claim 2, wherein the water soluble salt is sodium carbonate.

4. The method as claimed in claim 2, wherein the water soluble salt is potassium carbonate.

5. The method as claimed in claim 2, wherein the water soluble salt is sodium sulfide.

6. The method as claimed in claim 2, wherein the water soluble salt is sodium acetate.

7. The method as claimed in claim 2, wherein the water soluble salt is sodium bicarbonate.

8. The method as claimed in claim 2, wherein the salt is zinc acetate.

9. The method as claimed in claim 2, wherein the salt is antimony triacetate.

10. The method as claimed in claim 1, wherein mixed in the absence of water is the material containing poly(ethylene terephthalate) and ethylene glycol in a ratio by weight between 1:10 and 10:1.

11. The method as claimed in claim 10, wherein the ethylene glycol is either added at room temperature or pre-heated to a temperature of 100 and 190° C.

12. The method as claimed in claim 1, wherein the mixing in the absence of water is done in a propeller reactor at a propeller speed between 600 and 1600 revolutions per minute (rpm), at a temperature included between of 90 and 260° C. and over a period of time included between of 5 and 200 minutes.

13. The method as claimed in claim 12, wherein the mixing in the absence of water is done in a propeller reactor at a reaction speed between 800 and 1500 rpm, at a temperature included between 95 and 220° C. and over a period of time included between 10 and 140 minutes.

14. The method as claimed in claim 12, wherein in the mixing device the temperature to which formation of the soluble polymer fragments takes place is reached by virtue of a mechanical mixing action and/or by heating.

15. The method as claimed in claim 1, wherein the water added to the polymeric fragments is in a ratio by weight included between of 4 and 30 parts by weight of the water soluble polymer fragments.

16. The method as claimed in claim 1, wherein the solution having the polymer fragments mixed with water is filtered to provide a filtered solution, an acid stronger than the terephthalic acid is added to the filtered solution to precipitate salified poly(ethylene)terephthalate from the solution.

17. The method as claimed in claim 16, wherein the salified terephthalate is submitted to a further washing step.

18. The method as claimed in claim 1, wherein the solution is filtered and then submitted to hydrolysis carried out by heating and stirring of the solution, to obtain terephthalic acid in solution, in a salified form, and/or precipitated terephthalic acid, in an undissociated non salified form.

19. The method as claimed in claim 18, wherein the solution obtained after hydrolysis is added to a strong acid to obtain complete precipitation of the terephthalic acid.

20. The method as claimed in claim 1, wherein the solution is filtered and then is submitted to hydrolysis carried out by addition of a basic reagent, heating and stirring of the solution, to obtain a solution comprising terephthalic acid completely in a salified form.

21. The method as claimed in claim 20, wherein the solution comprising terephthalic acid completely in a salified form is added with a strong acid to obtain complete precipitation of the terephthalic acid in an undissociated form.

* * * * *